US00RE48501E

(19) United States
(12) Reissued Patent
McCormack et al.

(10) Patent Number: US RE48,501 E
(45) Date of Reissued Patent: Apr. 6, 2021

(54) CAGE SPINAL IMPLANT

(71) Applicant: PROVIDENCE MEDICAL TECHNOLOGY, INC., Walnut Creek, CA (US)

(72) Inventors: Bruce M. McCormack, San Francisco, CA (US); Edward Liou, Pleasanton, CA (US); Jeffrey D. Smith, Clayton, CA (US); David Michael Schummers, Oakland, CA (US)

(73) Assignee: Providence Medical Technology, Inc., Pleasanton, CA (US)

(21) Appl. No.: 29/608,669

(22) Filed: Jun. 23, 2017

Related U.S. Patent Documents

Reissue of:
(64) Patent No.: Des. 732,667
Issued: Jun. 23, 2015
Appl. No.: 29/435,385
Filed: Oct. 23, 2012

(51) LOC (13) Cl. ..... 24-02
(52) U.S. Cl.
USPC ..... D24/155
(58) Field of Classification Search
USPC ..... D24/155, 133, 135
(Continued)

(56) References Cited

U.S. PATENT DOCUMENTS 1,934,962 A 11/1933 Barry
2,708,376 A 5/1955 Hodgson
(Continued)

FOREIGN PATENT DOCUMENTS

DE G 93 04 368.6 5/2003
DE G9304368.6 U1 5/2003
(Continued)

OTHER PUBLICATIONS

US 7,063,700 B2, 06/2006, Michelson (withdrawn)
(Continued)

*Primary Examiner* — Philip S Hyder
(74) *Attorney, Agent, or Firm* — Dorsey & Whitney LLP

(57) CLAIM

The ornamental design for a cage spinal implant, as shown and described.

DESCRIPTION

[FIG. 1 is a right front perspective view of a cage spinal implant embodying our new design.]
[FIG. 2 is a front view thereof.]
[FIG. 3 is a right side view thereof.]
[FIG. 4 is a left side view thereof.]
[FIG. 5 is a rear view thereof.]
[FIG. 6 is a top view thereof, the bottom view being identical thereto.]
FIG. 7 is a right front perspective view of [another embodiment of] a cage spinal implant embodying our new design.
FIG. 8 is a front view of the embodiment shown in FIG. 7.
FIG. 9 is a right side view of the embodiment shown in FIG. 7.
FIG. 10 is a left side view of the embodiment shown in FIG. 7.
FIG. 11 is a rear view of the embodiment shown in FIG. 7; and,
FIG. 12 is a top view of the embodiment shown in FIG. 7, the bottom view being identical thereto.
The portions shown in broken lines in the figures are for illustrative purposes only and form no part of the claimed design.

1 Claim, 12 Drawing Sheets

Figure 1:
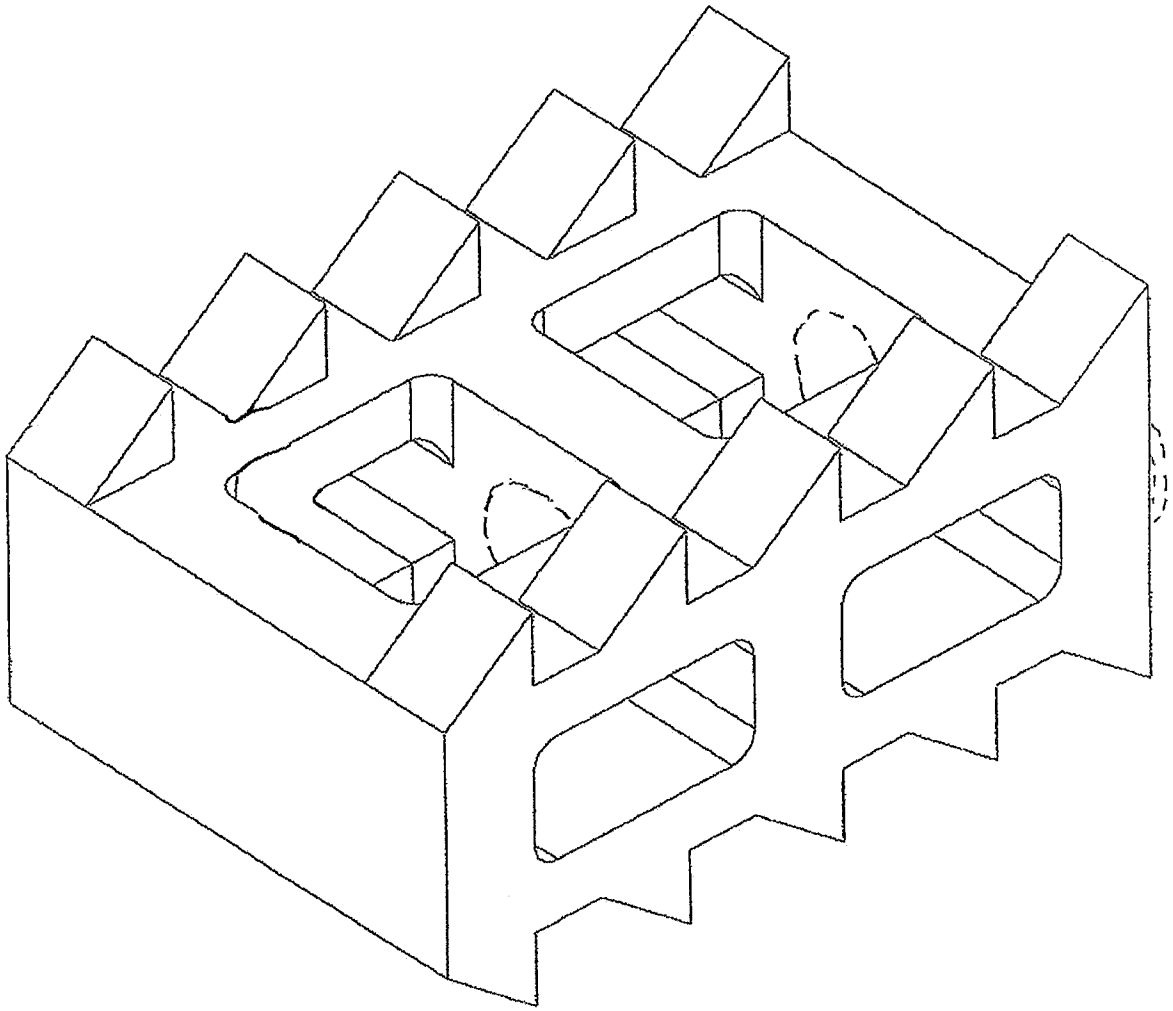
Figure 2:
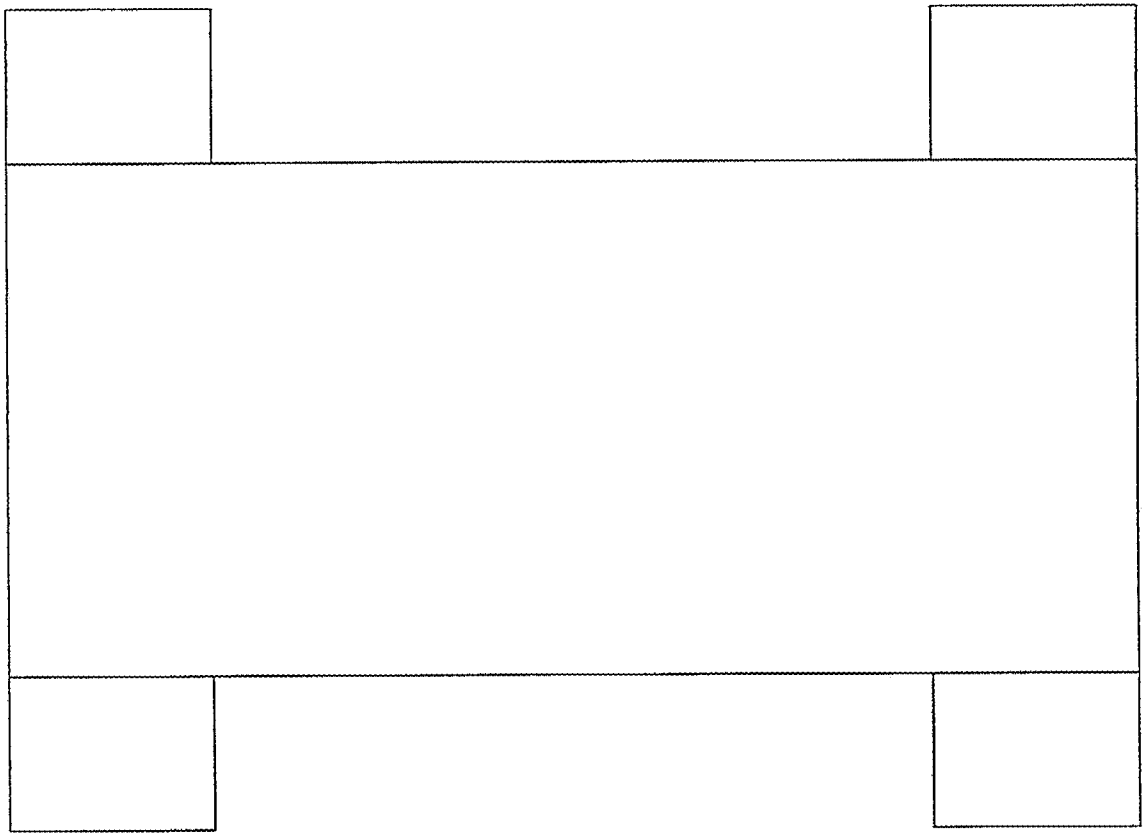
Figure 3:
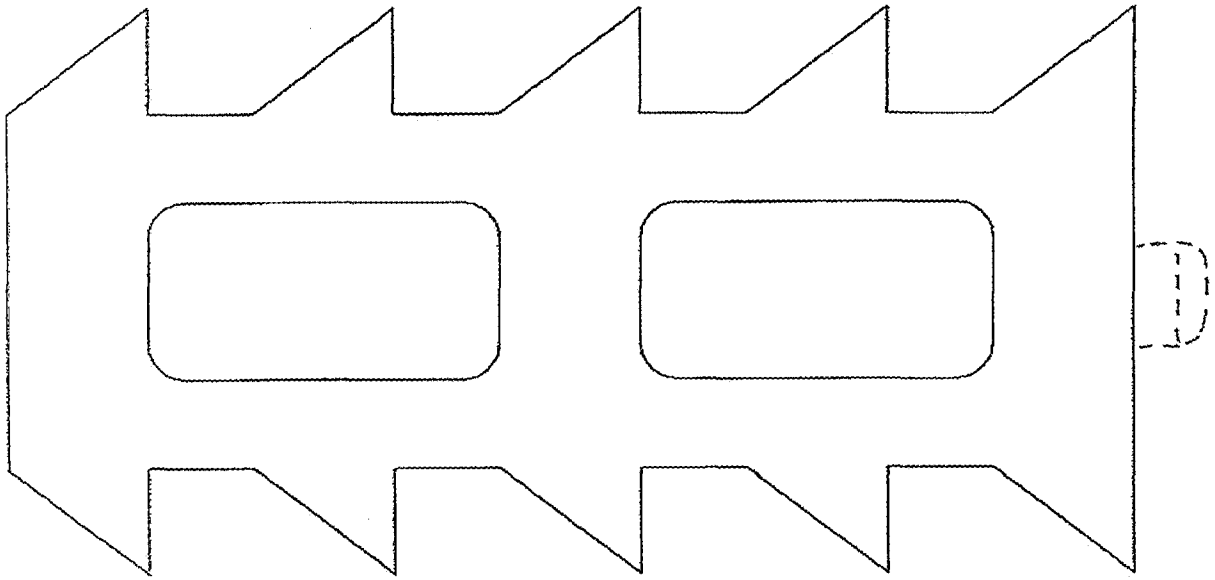
Figure 4:
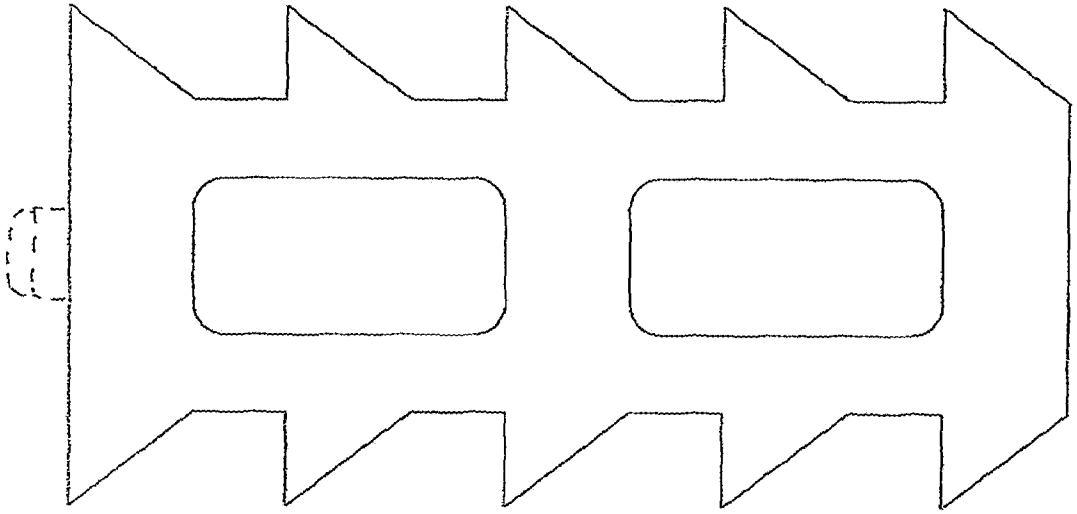
Figure 5:
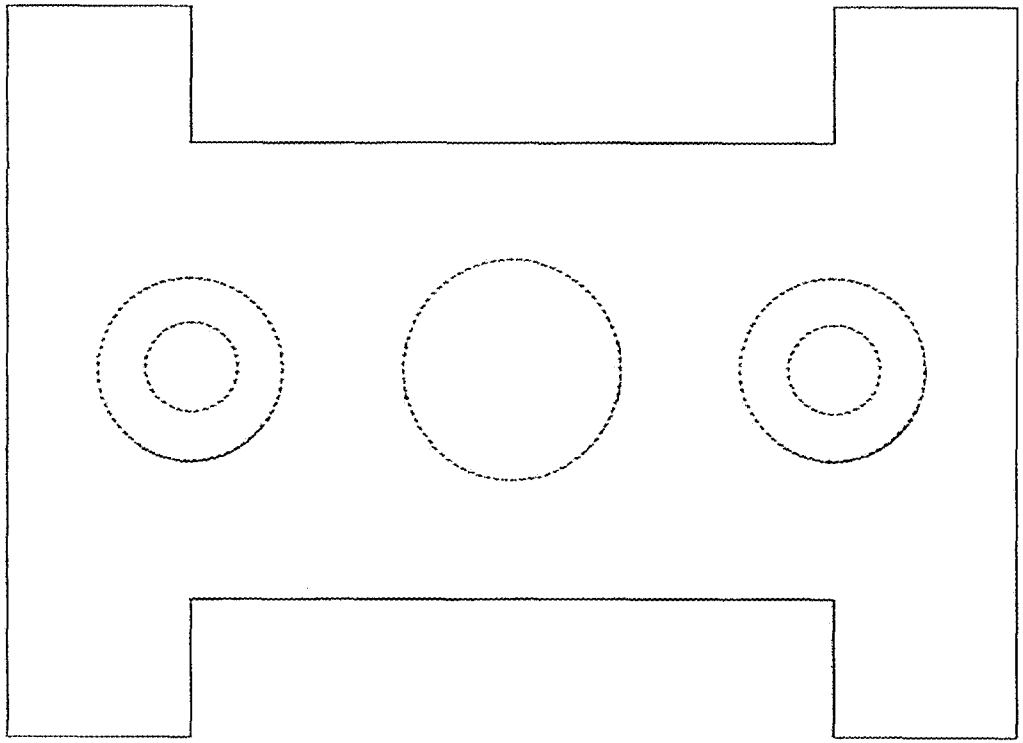
Figure 6:
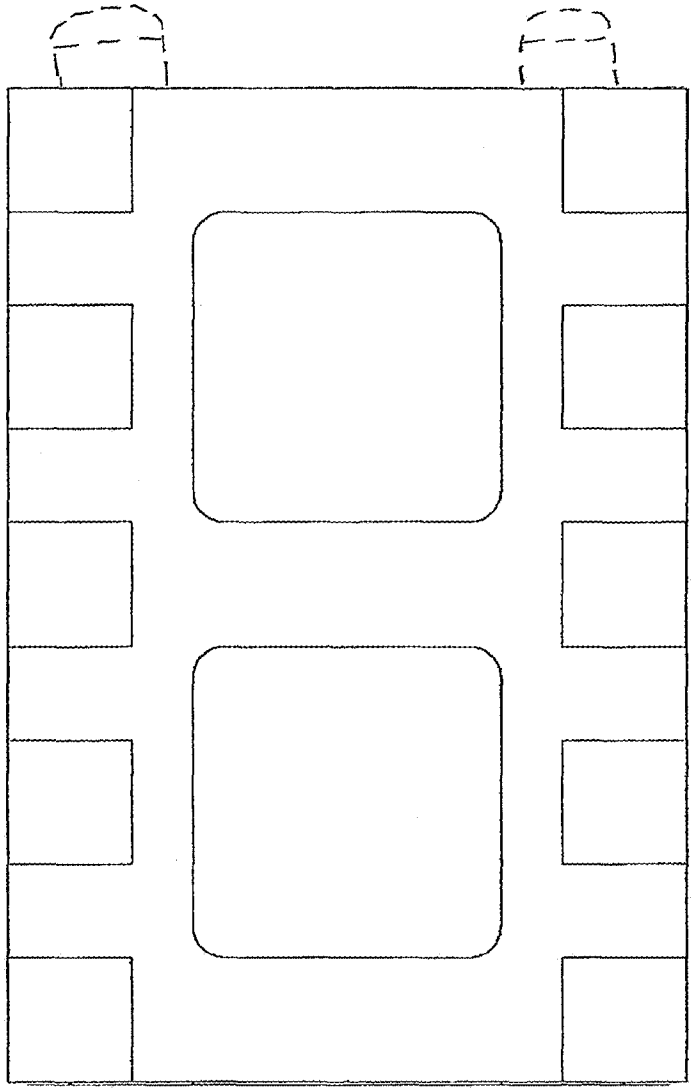

Matter enclosed in heavy brackets [ ] appears in the original patent but forms no part of this reissue; matter printed in italics indicates the additions made by reissue.

(58) Field of Classification Search
CPC ..... A61F 2/4611; A61F 2/422; A61F 2/447; A61F 2220/0025; A61F 2310/00023; A61F 2310/00017; A61F 2002/4475; A61F 2002/30841; A61F 2002/2835; A61F 2002/30904; A61F 2002/30785; A61F 2002/44; A61F 2002/30578
See application file for complete search history.

(56) References Cited

U.S. PATENT DOCUMENTS 2,984,241 A 5/1961 Carlson
3,486,505 A 12/1969 Morrison
4,479,491 A 10/1984 Martin
4,530,355 A 7/1985 Griggs
4,604,995 A 8/1986 Stephens et al.
4,772,287 A 9/1988 Ray et al.
4,877,020 A 10/1989 Vich
4,878,915 A 11/1989 Brantigan
5,015,247 A 5/1991 Michelson
5,026,373 A 6/1991 Ray et al.
5,100,405 A 3/1992 McLaren
5,135,528 A 8/1992 Winston
5,236,460 A 8/1993 Barber
5,443,514 A 8/1995 Steffee
5,484,437 A 1/1996 Michelson
5,489,307 A 2/1996 Kuslich et al.
5,505,732 A 4/1996 Michelson
5,527,312 A 6/1996 Ray
5,549,679 A 8/1996 Kuslich
5,554,191 A 9/1996 Lahille et al.
5,571,191 A 11/1996 Fitz
5,584,832 A 12/1996 Schlapfer
5,593,409 A 1/1997 Michelson
5,632,747 A 5/1997 Scarborough et al.
5,649,945 A 7/1997 Ray et al.
5,653,763 A 8/1997 Errico et al.
5,665,122 A 9/1997 Kambin
5,674,295 A 10/1997 Ray et al.
5,720,748 A 2/1998 Kuslich et al.
5,741,253 A 4/1998 Michelson
5,772,661 A 6/1998 Michelson
5,792,044 A 8/1998 Foley et al.
5,797,909 A 8/1998 Michelson
5,836,948 A 11/1998 Zuckerman et al.
5,879,353 A 3/1999 Terry
5,885,299 A 3/1999 Winslow et al.
5,891,147 A 4/1999 Moskovitz et al.
5,895,426 A 4/1999 Scarborough et al.
5,899,908 A 5/1999 Kuslich et al.
5,928,238 A 7/1999 Scarborough et al.
5,953,820 A 9/1999 Vasudeva
5,961,522 A 10/1999 Mehdizadeh
5,976,146 A 11/1999 Ogawa et al.
6,008,433 A * 12/1999 Stone ..... 623/20.14
6,033,405 A 3/2000 Winslow et al.
6,045,580 A 4/2000 Scarborough et al.
6,063,088 A 5/2000 Winslow
RE36,758 E 6/2000 Fitz
6,080,155 A 6/2000 Michelson
6,090,143 A 7/2000 Meriwether et al.
6,096,038 A 8/2000 Michelson
6,096,046 A 8/2000 Weiss
6,099,531 A 8/2000 Bonutti
6,102,950 A 8/2000 Vaccaro
6,113,602 A 9/2000 Sand
6,149,650 A 11/2000 Michelson
RE37,005 E 12/2000 Michelson et al.
6,159,245 A 12/2000 Meriwether et al.
6,176,882 B1 1/2001 Biedermann et al.
6,179,873 B1 1/2001 Zientek
6,190,388 B1 2/2001 Michelson et al.
6,190,414 B1 2/2001 Young et al.
6,193,757 B1 2/2001 Foley et al.
6,200,322 B1 3/2001 Branch et al.
6,210,412 B1 4/2001 Michelson
RE37,161 E 5/2001 Michelson et al.
6,224,595 B1 5/2001 Michelson
6,224,607 B1 5/2001 Michelson
6,224,630 B1 5/2001 Bao et al.
6,245,108 B1 6/2001 Biscup
6,248,110 B1 6/2001 Reiley et al.
D444,878 S * 7/2001 Walter ..... D24/155
D445,188 S * 7/2001 Walter ..... D24/155
6,264,656 B1 7/2001 Michelson
6,267,763 B1 7/2001 Castro
6,270,498 B1 8/2001 Michelson
6,283,966 B1 9/2001 Houfburg
6,315,795 B1 11/2001 Scarborough et al.
6,325,827 B1 12/2001 Lin
6,371,984 B1 4/2002 Van Dyke et al.
6,371,988 B1 4/2002 Pafford et al.
6,402,784 B1 6/2002 Wardlaw
6,423,063 B1 7/2002 Bonutti
6,423,083 B2 7/2002 Reiley et al.
6,425,919 B1 7/2002 Lambrecht
6,436,098 B1 8/2002 Michelson
6,436,142 B1 8/2002 Paes et al.
6,443,988 B2 9/2002 Felt et al.
6,451,023 B1 9/2002 Salazar et al.
6,454,807 B1 9/2002 Jackson
6,478,796 B2 11/2002 Zucherman et al.
6,500,206 B1 12/2002 Bryan
6,514,256 B2 2/2003 Zucherman et al.
6,530,955 B2 3/2003 Boyle et al.
6,558,390 B2 5/2003 Cragg
6,565,574 B2 5/2003 Michelson
6,565,605 B2 5/2003 Goble et al.
6,569,186 B1 5/2003 Winters et al.
6,575,919 B1 6/2003 Reiley et al.
6,575,979 B1 6/2003 Cragg
6,579,319 B2 6/2003 Goble et al.
6,582,432 B1 6/2003 Michelson
6,582,467 B1 6/2003 Teitelbaum et al.
6,607,530 B1 8/2003 Carl et al.
6,610,091 B1 8/2003 Reiley
6,626,905 B1 9/2003 Schmiel et al.
6,632,235 B2 10/2003 Weikel et al.
6,635,060 B2 10/2003 Hanson et al.
6,641,582 B1 11/2003 Hanson et al.
6,648,893 B2 11/2003 Dudasik
6,652,584 B2 11/2003 Michelson
6,663,647 B2 12/2003 Reiley et al.
6,666,866 B2 12/2003 Martz et al.
6,679,886 B2 1/2004 Weikel et al.
6,682,535 B2 1/2004 Hoogland
6,685,742 B1 2/2004 Jackson
6,709,458 B2 3/2004 Michelson
6,712,853 B2 3/2004 Kuslich
6,719,773 B1 4/2004 Boucher et al.
6,719,794 B2 4/2004 Gerber et al.
6,723,095 B2 4/2004 Hammerslag
6,733,534 B2 5/2004 Sherman
6,740,093 B2 5/2004 Hochschuler et al.
6,751,875 B2 6/2004 Jones
6,770,074 B2 8/2004 Michelson
6,793,679 B2 9/2004 Michelson
6,805,715 B2 10/2004 Reuter et al.
6,808,537 B2 10/2004 Michelson
6,823,871 B2 * 11/2004 Schmieding ..... 128/898
6,840,941 B2 1/2005 Rogers et al.
6,851,430 B2 2/2005 Tsou
6,875,213 B2 4/2005 Michelson
6,899,719 B2 5/2005 Reiley et al.
6,921,403 B2 7/2005 Cragg et al.
6,923,813 B2 8/2005 Phillips et al.
6,958,077 B2 10/2005 Suddaby
6,962,606 B2 11/2005 Michelson
6,964,686 B2 11/2005 Gordon
6,966,930 B2 11/2005 Arnin et al.
6,972,035 B2 12/2005 Michelson
6,974,478 B2 12/2005 Reiley et al.
6,979,333 B2 12/2005 Hammerslag
6,986,772 B2 1/2006 Michelson
7,001,385 B2 2/2006 Bonutti

(56) References Cited

U.S. PATENT DOCUMENTS 7,008,453 B1 3/2006 Michelson
7,033,362 B2 4/2006 McGahan et al.
7,033,392 B2 4/2006 Schmiel et al.
7,033,394 B2 4/2006 Michelson
7,066,961 B2 6/2006 Michelson
D524,443 S * 7/2006 Blain ..... D24/155
7,083,623 B2 8/2006 Michelson
7,090,698 B2 8/2006 Goble et al.
7,096,972 B2 8/2006 Orozco
7,101,398 B2 9/2006 Dooris et al.
7,115,128 B2 10/2006 Michelson
7,118,598 B2 10/2006 Michelson
7,128,760 B2 10/2006 Michelson
7,156,877 B2 1/2007 Lotz et al.
7,166,110 B2 1/2007 Yundt
7,175,023 B2 2/2007 Martin
7,179,263 B2 2/2007 Zdeblick et al.
7,207,991 B2 4/2007 Michelson
D541,940 S * 5/2007 Blain ..... D24/155
7,220,280 B2 5/2007 Kast et al.
7,255,703 B2 8/2007 Mujwid et al.
7,261,739 B2 8/2007 Ralph et al.
7,264,622 B2 9/2007 Michelson
7,273,498 B2 9/2007 Bianchi et al.
7,288,093 B2 10/2007 Michelson
7,291,149 B1 11/2007 Michelson
7,300,440 B2 11/2007 Zdeblick et al.
7,326,211 B2 2/2008 Padget et al.
7,326,214 B2 2/2008 Michelson
7,371,238 B2 5/2008 Soboleski et al.
7,399,303 B2 7/2008 Michelson
7,410,501 B2 8/2008 Michelson
7,431,722 B1 10/2008 Michelson
7,445,636 B2 11/2008 Michelson
7,452,359 B1 11/2008 Michelson
7,452,369 B2 11/2008 Barry
7,465,304 B1 12/2008 Haufe et al.
7,476,226 B2 1/2009 Weikel et al.
7,476,251 B2 1/2009 Zucherman et al.
7,479,160 B2 1/2009 Branch et al.
7,491,205 B1 2/2009 Michelson
7,491,240 B1 2/2009 Carver et al.
7,500,992 B2 3/2009 Li
7,517,358 B2 4/2009 Petersen
7,524,333 B2 4/2009 Lambrecht et al.
7,569,054 B2 8/2009 Michelson
7,569,057 B2 8/2009 Liu et al.
7,580,743 B2 8/2009 Bourlion et al.
7,591,851 B2 9/2009 Winslow et al.
7,601,170 B2 10/2009 Winslow et al.
7,608,077 B2 10/2009 Cragg et al.
7,608,107 B2 10/2009 Michelson
7,615,079 B2 11/2009 Flickinger et al.
7,618,451 B2 11/2009 Berez et al.
7,632,291 B2 12/2009 Stephens et al.
7,641,664 B2 1/2010 Pagano
7,645,232 B2 1/2010 Shluzas
7,648,509 B2 1/2010 Stark
7,648,523 B2 1/2010 Mirkovic et al.
7,655,027 B2 2/2010 Michelson
7,655,043 B2 2/2010 Peterman et al.
7,662,173 B2 2/2010 Cragg et al.
D611,147 S * 3/2010 Hanson et al. ..... D24/155
7,682,378 B2 3/2010 Truckai et al.
7,686,805 B2 3/2010 Michelson
7,686,807 B2 3/2010 Padget et al.
7,699,878 B2 4/2010 Pavlov et al.
D615,653 S * 5/2010 Horton ..... D24/155
7,708,761 B2 5/2010 Petersen
7,722,619 B2 5/2010 Michelson
D619,719 S 7/2010 Pannu
7,763,024 B2 7/2010 Bertagnoli et al.
7,763,050 B2 7/2010 Winslow et al.
7,776,090 B2 8/2010 Winslow et al.
D623,748 S * 9/2010 Horton et al. ..... D24/155
D623,749 S * 9/2010 Horton et al. ..... D24/155
7,789,898 B2 9/2010 Peterman
D627,468 S * 11/2010 Richter et al. ..... D24/155
7,824,431 B2 11/2010 McCormack
7,837,713 B2 11/2010 Petersen
7,846,183 B2 12/2010 Blain
7,846,184 B2 12/2010 Sasso et al.
7,850,733 B2 12/2010 Baynham et al.
7,862,589 B2 1/2011 Thramann
7,867,277 B1 1/2011 Tohmeh
D631,967 S * 2/2011 Horton ..... D24/155
7,879,098 B1 2/2011 Simmons
7,887,565 B2 2/2011 Michelson
7,892,261 B2 * 2/2011 Bonutti ..... 606/279
7,892,286 B2 2/2011 Michelson
7,896,803 B2 3/2011 Schara et al.
7,896,903 B2 3/2011 Link
7,901,439 B2 3/2011 Horton
7,914,530 B2 3/2011 Michelson
7,918,891 B1 4/2011 Curran et al.
7,922,729 B2 4/2011 Michelson
7,922,766 B2 4/2011 Grob et al.
7,935,136 B2 5/2011 Alamin et al.
7,938,857 B2 5/2011 Krueger et al.
7,942,903 B2 5/2011 Moskowitz et al.
7,988,712 B2 8/2011 Hale et al.
7,988,714 B2 8/2011 Puekert et al.
7,998,174 B2 8/2011 Malandain et al.
8,007,534 B2 8/2011 Michelson
8,029,540 B2 10/2011 Winslow et al.
8,043,334 B2 10/2011 Fisher et al.
8,052,728 B2 11/2011 Hestad
8,062,303 B2 11/2011 Berry et al.
8,066,705 B2 11/2011 Michelson
D650,481 S * 12/2011 Gottlieb et al. ..... D24/155
8,097,034 B2 1/2012 Michelson
8,100,944 B2 1/2012 Lauryssen et al.
D653,757 S * 2/2012 Binder ..... D24/155
8,114,158 B2 2/2012 Carl et al.
8,118,838 B2 2/2012 Winslow et al.
8,128,660 B2 3/2012 Mitchell et al.
8,133,261 B2 3/2012 Fisher et al.
8,142,503 B2 3/2012 Malone
8,147,553 B2 4/2012 Vresilovic et al.
8,162,981 B2 4/2012 Vestgaarden
8,172,877 B2 5/2012 Winslow et al.
8,177,872 B2 5/2012 Nelson et al.
8,197,513 B2 6/2012 Fisher et al.
8,206,418 B2 6/2012 Triplett et al.
8,267,966 B2 9/2012 McCormack et al.
D674,900 S * 1/2013 Janice et al. ..... D24/155
8,348,979 B2 1/2013 McCormack et al.
8,361,152 B2 1/2013 McCormack et al.
8,366,748 B2 2/2013 Kleiner
8,382,767 B2 2/2013 Wassinger et al.
D677,791 S * 3/2013 Danacioglu et al. ..... D24/155
8,394,107 B2 3/2013 Fanger et al.
8,394,129 B2 3/2013 Morgenstern Lopez et al.
D681,205 S * 4/2013 Farris et al. ..... D24/155
8,425,558 B2 4/2013 McCormack et al.
8,512,347 B2 8/2013 McCormack et al.
8,523,908 B2 9/2013 Malone
8,529,609 B2 9/2013 Helgerson et al.
8,623,054 B2 1/2014 McCormack et al.
8,668,722 B2 3/2014 Pavlov et al.
8,753,345 B2 6/2014 McCormack et al.
8,753,347 B2 6/2014 McCormack et al.
8,764,755 B2 7/2014 Michelson
8,828,062 B2 9/2014 McCormack et al.
8,834,530 B2 9/2014 McCormack
8,845,727 B2 9/2014 Gottlieb et al.
8,870,882 B2 10/2014 Kleiner
D723,690 S 3/2015 McCormack et al.
D723,691 S 3/2015 McCormack et al.
8,998,905 B2 4/2015 Marik et al.
9,005,288 B2 4/2015 McCormack et al.
9,011,492 B2 4/2015 McCormack et al.
D732,667 S 6/2015 McCormack et al.
9,186,193 B2 11/2015 Kleiner et al.

(56) References Cited

U.S. PATENT DOCUMENTS

D745,156 S 12/2015 McCormack et al.
9,211,198 B2 12/2015 Michelson
9,220,608 B2 12/2015 McKay
D750,249 S 2/2016 Grimberg, Jr. et al.
9,271,765 B2 3/2016 Blain
9,333,086 B2 5/2016 McCormack et al.
9,358,127 B2 6/2016 Duffield et al.
9,381,049 B2 7/2016 McCormack et al.
9,427,264 B2 8/2016 Kleiner et al.
9,504,583 B2 11/2016 Blain
9,622,791 B2 4/2017 McCormack et al.
9,622,873 B2 4/2017 McCormack
9,622,874 B2 4/2017 McCormack et al.
9,629,665 B2 4/2017 McCormack et al.
9,717,403 B2 8/2017 Kleiner et al.
10,039,649 B2 8/2018 McCormack et al.
10,111,670 B2 10/2018 Lorenzo et al.
10,149,673 B2 12/2018 McCormack et al.
10,172,721 B2 1/2019 McCormack et al.
D841,165 S 2/2019 McCormack et al.
10,201,375 B2 2/2019 McCormack et al.
10,206,787 B2 2/2019 Voellmicke
10,219,910 B2 3/2019 McCormack
10,226,285 B2 3/2019 McCormack et al.
10,238,501 B2 3/2019 McCormack et al.
10,456,175 B2 10/2019 McCormack et al.
10,568,666 B2 2/2020 McCormack et al.
10,588,672 B2 3/2020 Mccormack et al.
D884,895 S 5/2020 Mccormack et al.
D887,552 S 6/2020 Tanaka et al.
10,682,243 B2 6/2020 Phan et al.
2001/0004710 A1 6/2001 Felt et al.
2001/0047208 A1 11/2001 Michelson
2001/0053914 A1 12/2001 Landry et al.
2002/0026195 A1 2/2002 Layne et al.
2002/0068941 A1 6/2002 Hanson et al.
2002/0107519 A1 8/2002 Dixon
2002/0143343 A1 10/2002 Castro
2002/0147496 A1 10/2002 Belef et al.
2002/0147497 A1 10/2002 Belef et al.
2002/0165612 A1 11/2002 Gerber et al.
2002/0169471 A1 11/2002 Ferdinand
2002/0177866 A1 11/2002 Weikel et al.
2003/0023312 A1 1/2003 Thalgott
2003/0028251 A1 2/2003 Mathews
2003/0032962 A1 2/2003 McGahan et al.
2003/0033017 A1 2/2003 Lotz et al.
2003/0105526 A1* 6/2003 Bryant et al. ..... 623/16.11
2003/0109928 A1 6/2003 Pasquet et al.
2003/0139816 A1 7/2003 Michelson
2003/0144737 A1 7/2003 Sherman
2003/0149438 A1 8/2003 Nichols et al.
2003/0158553 A1 8/2003 Michelson
2003/0225416 A1 12/2003 Bonvallet et al.
2004/0059337 A1 3/2004 Hanson et al.
2004/0073217 A1 4/2004 Michelson
2004/0087948 A1 5/2004 Suddaby
2004/0087956 A1 5/2004 Weikel et al.
2004/0106999 A1 6/2004 Mathews
2004/0133277 A1 7/2004 Michelson
2004/0133280 A1 7/2004 Trieu
2004/0162562 A1 8/2004 Martz
2004/0215344 A1 10/2004 Hochschuler et al.
2005/0010294 A1 1/2005 Michelson
2005/0015097 A1 1/2005 Mujwid et al.
2005/0015149 A1 1/2005 Michelson
2005/0027358 A1 2/2005 Suddaby
2005/0033432 A1 2/2005 Gordon et al.
2005/0038511 A1 2/2005 Martz et al.
2005/0049705 A1 3/2005 Hale et al.
2005/0055096 A1 3/2005 Serhan et al.
2005/0065518 A1 3/2005 Michelson
2005/0065519 A1 3/2005 Michelson
2005/0065608 A1 3/2005 Michelson
2005/0065609 A1 3/2005 Wardlaw
2005/0080422 A1 4/2005 Otte et al.
2005/0090829 A1 4/2005 Martz et al.
2005/0090901 A1 4/2005 Studer
2005/0119680 A1 6/2005 Dykes
2005/0124993 A1 6/2005 Chappuis
2005/0149192 A1 7/2005 Zucherman et al.
2005/0159650 A1 7/2005 Raymond et al.
2005/0159746 A1 7/2005 Grob et al.
2005/0177240 A1 8/2005 Blain
2005/0182417 A1 8/2005 Pagano
2005/0216018 A1 9/2005 Sennett
2005/0234455 A1 10/2005 Binder et al.
2005/0240188 A1 10/2005 Chow et al.
2005/0251146 A1 11/2005 Martz et al.
2005/0251257 A1 11/2005 Mitchell et al.
2005/0267480 A1 12/2005 Suddaby
2006/0004367 A1 1/2006 Alamin et al.
2006/0015184 A1* 1/2006 Winterbottom et al. .. 623/18.11
2006/0036243 A1 2/2006 Sasso et al.
2006/0036247 A1 2/2006 Michelson
2006/0036323 A1 2/2006 Carl et al.
2006/0041311 A1 2/2006 McLeer
2006/0058793 A1 3/2006 Michelson
2006/0058878 A1 3/2006 Michelson
2006/0069442 A1 3/2006 Michelson
2006/0079905 A1 4/2006 Beyar et al.
2006/0079962 A1 4/2006 Michelson
2006/0085068 A1 4/2006 Barry
2006/0085074 A1 4/2006 Raiszadeh
2006/0095028 A1 5/2006 Bleich
2006/0095036 A1 5/2006 Hammerslag
2006/0111779 A1 5/2006 Peterson
2006/0111780 A1 5/2006 Petersen
2006/0111781 A1 5/2006 Petersen
2006/0142762 A1 6/2006 Michelson
2006/0149289 A1 7/2006 Winslow et al.
2006/0184172 A1 8/2006 Michelson
2006/0189991 A1 8/2006 Bickley
2006/0190081 A1 8/2006 Kraus et al.
2006/0195109 A1 8/2006 McGahan et al.
2006/0200137 A1 9/2006 Soboleski et al.
2006/0200138 A1 9/2006 Michelson
2006/0200139 A1 9/2006 Michelson
2006/0206118 A1 9/2006 Kim et al.
2006/0217812 A1 9/2006 Lambrecht et al.
2006/0229627 A1 10/2006 Hunt et al.
2006/0235391 A1 10/2006 Sutterlin, III
2006/0241597 A1 10/2006 Mitchell et al.
2006/0241626 A1 10/2006 McGahan et al.
2006/0241758 A1 10/2006 Peterman et al.
2006/0247632 A1 11/2006 Winslow et al.
2006/0247633 A1 11/2006 Winslow et al.
2006/0247650 A1 11/2006 Yerby et al.
2006/0259142 A1 11/2006 Dooris et al.
2006/0271195 A1 11/2006 Thramann
2006/0276790 A1 12/2006 Dawson et al.
2006/0276801 A1 12/2006 Yerby et al.
2006/0276897 A1 12/2006 Winslow et al.
2006/0293663 A1 12/2006 Walkenhorst et al.
2007/0016195 A1 1/2007 Winslow et al.
2007/0016196 A1 1/2007 Winslow et al.
2007/0016218 A1 1/2007 Winslow et al.
2007/0032871 A1 2/2007 Michelson
2007/0043362 A1 2/2007 Malandain et al.
2007/0050031 A1 3/2007 Khosrowshahi
2007/0055245 A1 3/2007 Sasso et al.
2007/0055263 A1 3/2007 Way et al.
2007/0073402 A1 3/2007 Vresilovic et al.
2007/0083265 A1 4/2007 Malone
2007/0123863 A1 5/2007 Winslow et al.
2007/0123888 A1 5/2007 Bleich et al.
2007/0135814 A1 6/2007 Farris
2007/0135921 A1 6/2007 Park
2007/0149976 A1 6/2007 Hale et al.
2007/0149983 A1 6/2007 Link
2007/0150061 A1 6/2007 Trieu
2007/0161991 A1 7/2007 Altarac et al.
2007/0162138 A1 7/2007 Heinz
2007/0179617 A1 8/2007 Brown et al.

(56) References Cited

U.S. PATENT DOCUMENTS

2007/0179619 A1 8/2007 Grob et al.
2007/0191861 A1 8/2007 Allard et al.
2007/0225721 A1 9/2007 Thelen et al.
2007/0225812 A1 9/2007 Gill
2007/0244483 A9 10/2007 Winslow et al.
2007/0250167 A1 10/2007 Bray et al.
2007/0276491 A1 11/2007 Ahrens
2007/0282441 A1 12/2007 Stream et al.
2007/0288014 A1 12/2007 Shadduck et al.
2007/0293949 A1 12/2007 Salerni et al.
2007/0299451 A1 12/2007 Tulkis
2008/0015581 A1 1/2008 Eckman et al.
2008/0021457 A1 1/2008 Anderson et al.
2008/0021464 A1 1/2008 Morin et al.
2008/0045970 A1 2/2008 Saidha et al.
2008/0058954 A1 3/2008 Trieu
2008/0065219 A1 3/2008 Dye
2008/0097436 A1 4/2008 Culbert et al.
2008/0108996 A1 5/2008 Padget et al.
2008/0140207 A1 6/2008 Olmos et al.
2008/0154377 A1 6/2008 Voellmicke
2008/0161810 A1 7/2008 Melkent
2008/0161929 A1 7/2008 McCormack et al.
2008/0167657 A1 7/2008 Greenhalgh
2008/0177311 A1 7/2008 Winslow et al.
2008/0208341 A1 8/2008 McCormack et al.
2008/0216846 A1 9/2008 Levin
2008/0234677 A1 9/2008 Dahners et al.
2008/0234758 A1 9/2008 Fisher et al.
2008/0249571 A1 10/2008 Sasso et al.
2008/0255564 A1 10/2008 Michelson
2008/0255618 A1 10/2008 Fisher et al.
2008/0255622 A1 10/2008 Mickiewicz et al.
2008/0255666 A1 10/2008 Fisher et al.
2008/0255667 A1 10/2008 Horton
2008/0275455 A1 11/2008 Berry et al.
2008/0287955 A1 11/2008 Michelson
2008/0300685 A1 12/2008 Carls et al.
2008/0306537 A1 12/2008 Culbert
2008/0312744 A1 12/2008 Vresilovic et al.
2009/0131986 A1 5/2009 Lee et al.
2009/0138053 A1 5/2009 Assell et al.
2009/0177205 A1 7/2009 McCormack et al.
2009/0177215 A1 7/2009 Stack et al.
2009/0177237 A1 7/2009 Zucherman et al.
2009/0234397 A1 9/2009 Petersen
2009/0248076 A1 10/2009 Reynolds et al.
2009/0263461 A1 10/2009 McKay
2009/0270929 A1 10/2009 Suddaby et al.
2009/0275994 A1 11/2009 Phan et al.
2009/0306671 A1 12/2009 McCormack et al.
2009/0312763 A1 12/2009 McCormack et al.
2010/0069912 A1 3/2010 McCormack et al.
2010/0082065 A1 4/2010 Butler et al.
2010/0086185 A1 4/2010 Weiss
2010/0093829 A1 4/2010 Gorman
2010/0111829 A1 5/2010 Drapeau et al.
2010/0114105 A1 5/2010 Butters et al.
2010/0114318 A1 5/2010 Gittings et al.
2010/0145391 A1 6/2010 Kleiner
2010/0145459 A1 6/2010 Mcdonough et al.
2010/0191241 A1 7/2010 McCormack et al.
2010/0211104 A1 8/2010 Moumene et al.
2010/0286783 A1 11/2010 Lechmann et al.
2011/0004247 A1 1/2011 Lechmann et al.
2011/0022089 A1 1/2011 Assell et al.
2011/0054613 A1 3/2011 Hansen
2011/0077686 A1 3/2011 Mishra et al.
2011/0082548 A1 4/2011 Assell et al.
2011/0144755 A1 6/2011 Baynham et al.
2011/0184470 A1 7/2011 Gorek et al.
2011/0190821 A1 8/2011 Chin et al.
2011/0245930 A1 10/2011 Alley et al.
2011/0295327 A1 12/2011 Moskowitz et al.
2011/0307061 A1 12/2011 Assell et al.
2012/0010659 A1 1/2012 Angert et al.
2012/0010662 A1 1/2012 O'Neil et al.
2012/0010669 A1 1/2012 O'Neil et al.
2012/0065613 A1 3/2012 Pepper et al.
2012/0130496 A1 5/2012 Duffield et al.
2012/0143334 A1* 6/2012 Boyce et al. ..... 623/16.11
2012/0179259 A1 7/2012 Mcdonough et al.
2012/0215259 A1 8/2012 Cannestra
2012/0226358 A1 9/2012 Kleiner
2012/0265250 A1 10/2012 Ali
2012/0283776 A1 11/2012 Mishra
2012/0323242 A1 12/2012 Tsuang et al.
2013/0006364 A1 1/2013 McCormack et al.
2013/0012994 A1 1/2013 McCormack et al.
2013/0013070 A1 1/2013 McCormack et al.
2013/0018474 A1 1/2013 McCormack et al.
2013/0023889 A1 1/2013 Blain et al.
2013/0023995 A1 1/2013 McCormack et al.
2013/0023996 A1 1/2013 McCormack et al.
2013/0030440 A1 1/2013 McCormack et al.
2013/0030532 A1 1/2013 McCormack et al.
2013/0110168 A1 5/2013 McCormack et al.
2013/0110243 A1 5/2013 Patterson et al.
2013/0123922 A1 5/2013 McCormack et al.
2013/0144389 A1* 6/2013 Bonutti ..... 623/17.16
2013/0226239 A1 8/2013 Altarac et al.
2013/0253649 A1 9/2013 Davis
2013/0274763 A1 10/2013 Drapeau et al.
2013/0310839 A1 11/2013 McCormack et al.
2013/0310878 A1 11/2013 McCormack et al.
2013/0310943 A1 11/2013 McCormack et al.
2013/0317548 A1 11/2013 Malone
2013/0338720 A1 12/2013 Kleiner
2014/0012318 A1 1/2014 Goel
2014/0025113 A1 1/2014 McCormack et al.
2014/0100657 A1 4/2014 McCormack et al.
2014/0135930 A1 5/2014 Georges
2014/0172103 A1 6/2014 O'neil et al.
2014/0228959 A1 8/2014 Niemiec et al.
2014/0275801 A1 9/2014 Menchaca et al.
2014/0296916 A1 10/2014 McCormack et al.
2014/0379087 A1 12/2014 McCormack
2015/0025635 A1 1/2015 Laubert
2015/0100129 A1 4/2015 Waugh et al.
2015/0201977 A1 7/2015 McCormack et al.
2015/0328005 A1 11/2015 Padovani et al.
2015/0328010 A1 11/2015 Martynova et al.
2015/0342648 A1 12/2015 Mccormack et al.
2015/0342649 A1 12/2015 McCormack et al.
2016/0008040 A1 1/2016 McCormack et al.
2016/0242754 A1 8/2016 McCormack et al.
2016/0250035 A1 9/2016 De Villiers et al.
2017/0027713 A1 2/2017 Kleiner
2017/0135733 A1 5/2017 Donner et al.
2017/0189199 A1 7/2017 Maier et al.
2017/0216044 A1 8/2017 McCormack
2017/0281360 A1 10/2017 Seifert
2017/0348027 A1 12/2017 McCormack et al.
2017/0354444 A1 12/2017 McCormack et al.
2017/0360571 A1 12/2017 Mesiwala
2018/0161077 A1 6/2018 McCormack et al.
2018/0303631 A1 10/2018 Phan et al.
2019/0209151 A1 7/2019 McCormack et al.
2019/0239932 A1 8/2019 McCormack et al.
2019/0240041 A1 8/2019 McCormack et al.
2019/0247099 A1 8/2019 McCormack et al.
2019/0247614 A1 8/2019 Hart et al.
2019/0307571 A1 10/2019 McCormack
2019/0307572 A1 10/2019 McCormack et al.
2019/0350626 A1 11/2019 McCormack et al.
2020/0085475 A1 3/2020 McCormack et al.
2020/0155205 A1 5/2020 Tanaka et al.
2020/0289285 A1 9/2020 Siemionow et al.

FOREIGN PATENT DOCUMENTS

EP 2272436 A1 1/2011
FR 2722980 A1 2/1996
JP 2014516268 A 7/2014

(56) References Cited

FOREIGN PATENT DOCUMENTS

| | | | |
|---|---|---|---|
| WO | 9641582 | A1 | 12/1996 |
| WO | 9829026 | A2 | 7/1998 |
| WO | WO 99/49818 | A1 | 10/1999 |
| WO | 00/35388 | | 6/2000 |
| WO | WO 00/35388 | A1 | 6/2000 |
| WO | WO 00/53126 | A1 | 9/2000 |
| WO | WO 01/01895 | A1 | 1/2001 |
| WO | 2002/038062 | | 5/2002 |
| WO | WO 02/34120 | A2 | 5/2002 |
| WO | WO 02/38062 | A2 | 5/2002 |
| WO | 02/076335 | | 10/2002 |
| WO | WO 02/076335 | A2 | 10/2002 |
| WO | 2006/058221 | | 6/2006 |
| WO | WO 2006/058221 | A2 | 6/2006 |
| WO | WO 2006/096803 | A2 | 9/2006 |
| WO | 2006/130791 | | 12/2006 |
| WO | WO 2006/130791 | A2 | 12/2006 |
| WO | WO 2006/135792 | A1 | 12/2006 |
| WO | 2007120903 | A2 | 10/2007 |
| WO | WO 2007/120903 | A1 | 10/2007 |
| WO | 2008/083349 | A1 | 7/2008 |
| WO | 2008127978 | A2 | 10/2008 |
| WO | 2008153732 | A1 | 12/2008 |
| WO | 2009/089367 | | 7/2009 |
| WO | 2009/148619 | | 12/2009 |
| WO | 2010/030994 | | 3/2010 |
| WO | 2010/074714 | | 7/2010 |
| WO | 2010107692 | A1 | 9/2010 |
| WO | 2011050140 | A1 | 4/2011 |
| WO | 2013043584 | A2 | 3/2013 |
| WO | 2014188280 | A2 | 11/2014 |
| WO | 2016/049784 | | 4/2016 |
| WO | 2020/033811 | A2 | 2/2020 |

OTHER PUBLICATIONS

Goel et al., "Facetal distraction as treatment for single- and multilevel cervical spondylotic radiculopathy and myelopathy: a preliminary report," J Neurosurg Spine, Jun. 2011, pp. 689-696, vol. 14.
Press Release , Interventional Spine, Inc., Interventional Spine, Inc. Introduces the PERPOS Fusion Facet Prep Kit, Oct. 14, 2008 (1 page).
Press Release, minSURG Corp., Orthopedic Development Corporation's TruFUSE Procedure Tops 1,750 Patients in First Year, Sep. 24, 2007 (1 page).
Press Release , Interventional Spine, Inc., FDA Grants Conditional Approval to Interventional Spine's PercuDyn System IDE Application, Jul. 1, 2008 (1 page).
Stein et al., "Percutaneous Facet Joint Fusion: Preliminary Experience," Journal of Vascular and Interventional Radiology, Jan.-Feb. 1993, pp. 69-74, vol. 4, No. 1.
Advisory Action, U.S. Appl. No. 12/317,682, dated Apr. 6, 2012, 3 pages.
Advisory Action, U.S. Appl. No. 12/455,814, dated Aug. 16, 2012, 3 pages.
Amendment and Response to Office Action, U.S. Appl. No. 12/110,548, filed May 5, 2009, 11 pages.
Amendment, U.S. Appl. No. 11/618,619, filed May 5, 2008, 10 pages.
Corrected Response to Restriction Requirement, U.S. Appl. No. 12/317,682, filed Sep. 2, 2011, 15 pages.
Final Office Action, U.S. Appl. No. 11/618,619, mailed Aug. 8, 2008, 10 pages.
Final Office Action, U.S. Appl. No. 12/110,548, mailed Feb. 26, 2010, 4 pages.
Final Office Action, U.S. Appl. No. 12/317,682, mailed Feb. 10, 2012, 8 pages.
Final Office Action, U.S. Appl. No. 12/350,609, mailed Apr. 25, 2012, 10 pages.
Final Office Action, U.S. Appl. No. 12/455,814, mailed Jun. 6, 2012, 12 pages.
Final Office Action, U.S. Appl. No. 12/559,193, mailed Feb. 13, 2013, 10 pages.
Final Office Action, U.S. Appl. No. 12/653,283, mailed Mar. 21, 2012, 8 pages.
Final Office Action, U.S. Appl. No. 12/653,283, mailed Nov. 19, 2012, 8 pages.
Goel, Atul et al., Facetal Distraction as Treatment for Single- and Multilevel Cervical spondylotic Radiculopathy and Myelopathy: A Preliminary Report. J Neurosurg Spine 14:689-696, Jun. 2011; published online Mar. 18, 2011; DOI: 10.3171/2011.2.SPINE10601.
International Search Report and WO, International patent application No. PCT/US2009/056841, dated Apr. 9, 2010.
International Search Report and WO, PCT/US2009/006478, dated Jun. 29, 2010.
International Search Report and Written Opinion, International patent application No. PCT/US07/89146, dated Nov. 3, 2008.
International Search Report and Written Opinion, International patent application No. PCT/US2009/030461, dated Aug. 17, 2009.
International Search Report and Written Opinion, International patent application No. PCT/US2009/003423, dated Dec. 14, 2009.
Interview Summary, U.S. Appl. No. 11/618,619, mailed Mar. 18, 2008, 3 pages.
Medtronic, Cervical FacetLift ID/S Indirect Decompression and Stabilization technique using Cornerstone Facet MicroGrafts, Surgical Technique. Copyright 2012 Medtronic Sofamor Danek USA, Inc.
Non-Final Office Action, U.S. Appl. No. 11/618,619, mailed Jan. 3, 2008, 12 pages.
Non-Final Office Action, U.S. Appl. No. 12/110,548, mailed Feb. 17, 2009, 11 pages.
Nonfinal Office Action, U.S. Appl. No. 12/317,682, dated sep. 15, 2011, 25 pages.
Non-final Office Action, U.S. Appl. No. 12/350,609, dated Oct. 18, 2011, 27 pages.
Non-Final Office Action, U.S. Appl. No. 12/455,814, dated Jan. 24, 2012, 30 pages.
Non-Final Office Action, U.S. Appl. No. 12/559,193, mailed Sep. 18, 2012, 26 pages.
Non-Final Office Action, U.S. Appl. No. 12/653,283, mailed Feb. 10, 2012, 7 pages.
Non-Final Office Action, U.S. Appl. No. 12/653,283, mailed Jul. 18, 2012, 5 pages.
Nonfinal Office Action, U.S. Appl. No. 12/653,283, dated Aug. 9, 2011, 20 pages.
Non-Final Office Action, U.S. Appl. No. 12/889,122, dated Mar. 29, 2012, 20 pages.
Notice of Allowance, U.S. Appl. No. 12/110,548, mailed Mar. 29, 2010, 5 pages.
Notice of Allowance, U.S. Appl. No. 12/110,548, mailed Jul. 14, 2010, 10 pages.
Notice of Allowance, U.S. Appl. No. 12/317,682, mailed May 11, 2012, 10 pages.
Notice of Allowance, U.S. Appl. No. 12/455,814, mailed Oct. 2, 2012, 6 pages.
Notice of Allowance, U.S. Appl. No. 12/653,283, mailed Feb. 28, 2013, 10 pages.
Notice of Allowance, U.S. Appl. No. 12/889,122, mailed Sep. 25, 2012, 7 pages.
Notice of Non-Responsive Amendment, U.S. Appl. No. 12/317,682, dated Aug. 8, 2011, 2 pages.
Office Action (Quayle), U.S. Appl. No. 12/653,283, dated Dec. 22, 2011, 8 pages.
Office Action (Restriction), U.S. Appl. No. 12/317,682, dated Apr. 22, 2011, 14 pages.
Office Action (Restriction), U.S. Appl. No. 12/350,609, dated Jun. 14, 2011, 6 pages.
Office Action (Restriction), U.S. Appl. No. 12/455,814, dated Apr. 20, 2011, 14 pages.
Office Action (Restriction), U.S. Appl. No. 12/653,283, dated Jun. 24, 2011, 9 pages.
Partial International Search Report, International patent application No. PCT/US2009/030461, dated May 13, 2009.

(56) References Cited

OTHER PUBLICATIONS

Partial International Search Report, International patent application No. PCT/US2009/003423, dated Sep. 14, 2009.
Partial International Search Report, International patent application No. PCT/US2009/056841, dated Dec. 10, 2009.
Partial International Search Report, International patent application No. PCT/US2009/006478, dated Apr. 7, 2010.
Press Release , Interventional Spine, Inc., FDA Grants Conditional Approval to Interventional Spine's PercuDyn System IDE Application (Jul. 1, 2008).
Press Release , Interventional Spine, Inc., Interventional Spine, Inc. Introduces the PERPOS Fusion Facet Prep Kit (Oct. 14, 2008).
Press Release, minSURG Corp., Orthopedic Development Corporation's TruFUSE Procedure Tops 1,750 Patients in First Year (Sep. 24, 2007).
RCE/Amendment, U.S. Appl. No. 12/350,609, filed Jul. 24, 2012, 19 pages.
Response to Advisory Action, U.S. Appl. No. 12/317,682, filed Apr. 24, 2012, 4 pages.
Response to Advisory Action, U.S. Appl. No. 12/455,814, filed Sep. 5, 2012, 6 pages.
Response to Final Office Action, U.S. Appl. No. 12/317,682, filed Mar. 22, 2012, 17 pages.
Response to Final Office Action, U.S. Appl. No. 12/455,814, filed Aug. 6, 2012, 13 pages.
Response to Final Office Action, U.S. Appl. No. 12/559,193, filed Apr. 12, 2013, 8 pages.
Response to Final Office Action, U.S. Appl. No. 12/653,283, filed Jun. 15, 2012, 7 pages.
Response to Final Office Action, U.S. Appl. No. 12/653,283, filed Feb. 19, 2013, 5 pages.
Response to Non-Final Office Action and Terminal Disclaimer, U.S. Appl. No. 12/889,122, filed Jun. 27, 2012, 8 pages.
Response to Non-Final Office Action, U.S. Appl. No. 12/317,682, filed Dec. 13, 2011, 19 pages.
Response to Non-Final Office Action, U.S. Appl. No. 12/350,609, filed Feb. 17, 2012, 16 pages.
Response to Non-Final Office Action, U.S. Appl. No. 12/455,814, filed Apr. 24, 2012, 15 pages.
Response to Non-Final Office Action, U.S. Appl. No. 12/653,283, filed Dec. 6, 2011, 14 pages.
Response to Non-Final Office Action, U.S. Appl. No. 12/653,283, filed Mar. 8, 2012, 9 pages.
Response to Non-Final Office Action, U.S. Appl. No. 12/653,283, filed Oct. 18, 2012, 6 pages.
Response to Non-Final Office Action, U.S. Appl. No. 12/599,193, filed Dec. 13, 2012, 7 pages.
Response to Quayle Action, U.S. Appl. No. 12/653,283, filed Feb. 1, 2012, 3 pages.
Response to Restriction Requirement, U.S. Appl. No. 12/350,609, filed Aug. 15, 2011, 14 pages.
Response to Restriction, U.S. Appl. No. 12/317,682, filed May 16, 2011, 15 pages.
Response to Restriction, U.S. Appl. No. 12/455,814, filed May 16, 2011, 10 pages.
Response to Restriction, U.S. Appl. No. 12/559,193, filed Jul. 17, 2012, 6 pages.
Response to Restriction, U.S. Appl. No. 12/653,283, filed Jul. 22, 2011, 8 pages.
Restriction Requirement, U.S. Appl. No. 12/559,193, dated Apr. 18, 2012, 10 pages.
Advisory Action, U.S. Appl. No. 13/614,372, dated Feb. 26, 2014, 6 pages.
Final Office Action, U.S. Appl. No. 12/350,609, dated Feb. 10, 2014, 16 pages.
Final Office Action, U.S. Appl. No. 13/614,372, dated Oct. 25, 2013, 9 pages.
Final Office Action, U.S. Appl. No. 13/614,508, dated Dec. 23, 2013, 12 pages.
Final Office Action, U.S. Appl. No. 13/627,825, dated Dec. 4, 2013, 8 pgs.
Final Office Action, U.S. Appl. No. 13/627,850, dated Dec. 30, 2013, 12 pages.
Final Office Action, U.S. Appl. No. 13/627,865, dated Dec. 4, 2013, 10 pages.
International Search Report and Written Opinion, PCT/US2013/073744, dated Mar. 31, 2014, 11 pages.
Miscellaneous Office Action, U.S. Appl. No. 13/614,577, dated Apr. 23, 2014, 2 pages.
Non-Final Office Action, U.S. Appl. No. 29/435,381, dated Oct. 7, 2013, 20 pages.
Non-Final Office Action, U.S. Appl. No. 12/350,609, dated Oct. 10, 2013, 17 pages.
Non-Final Office Action, U.S. Appl. No. 13/614,372, mailed Jun. 26, 2013, 22 pages.
Non-Final Office Action, U.S. Appl. No. 13/614,508, mailed Jul. 17, 2013, 25 pages.
Non-Final Office Action, U.S. Appl. No. 13/614,577, mailed Jul. 19, 2013, 22 pages.
Non-Final Office Action, U.S. Appl. No. 13/614,577, dated Dec. 5, 2013, 10 pages.
Non-Final Office Action, U.S. Appl. No. 13/627,825, mailed Jul. 19, 2013, 22 pages.
Non-Final Office Action, U.S. Appl. No. 13/627,850, mailed Jul. 25, 2013, 23 pages.
Non-Final Office Action, U.S. Appl. No. 13/627,865, mailed Jul. 26, 2013, 25 pages.
Non-Final Office Action, U.S. Appl. No. 13/722,802, mailed Sep. 26, 2013, 8 pages.
Non-Final Office Action, U.S. Appl. No. 29/448,467, dated Oct. 2, 2013, 8 pages.
Non-Final Office Action, U.S. Appl. No. 29/448,474, dated Oct. 2, 2013, 8 pages.
Notice of Allowance, U.S. Appl. No. 12/559,193, mailed Apr. 22, 2013, 8 pages.
Notice of Allowance, U.S. Appl. No. 13/614,372, dated Apr. 16, 2014, 18 pages.
Notice of Allowance, U.S. Appl. No. 13/627,812, mailed Aug. 30, 2013, 25 pages.
Notice of Allowance, U.S. Appl. No. 13/627,825, dated Feb. 27, 2014, 12 pages.
Notice of Allowance, U.S. Appl. No. 13/627,865, dated Feb. 20, 2014, 9 pages.
Response to Final Office Action, U.S. Appl. No. 13/614,372, dated Dec. 20, 2013, 11 pages.
Response to Final Office Action, U.S. Appl. No. 13/627,825, dated Jan. 28, 2014, 9 pages.
Response to Final Office Action, U.S. Appl. No. 13/627,850, dated Mar. 31, 2014, 9 pages.
Response to Final Office Action, U.S. Appl. No. 13/627,865, dated Feb. 4, 2014, 9 pages.
Response to Non-Final Office Action and Terminal Disclaimer, U.S. Appl. No. 13/627,850, filed Oct. 25, 2013, 11 pages.
Response to Non-Final Office Action, U.S. Appl. No. 29/435,381, dated Mar. 4, 2014, 6 pages.
Response to Non-Final Office Action, U.S. Appl. No. 12/350,609, dated Jan. 10, 2014, 22 pages.
Response to Non-Final Office Action, U.S. Appl. No. 13/614,372, filed Sep. 26, 2013, 13 pages.
Response to Non-Final Office Action, U.S. Appl. No. 13/614,508, filed Oct. 17, 2013, 12 pages.
Response to Non-final Office Action, U.S. Appl. No. 13/614,577, filed Oct. 21, 2013, 10 pages.
Response to Non-Final Office Action, U.S. Appl. No. 13/614,577, dated Apr. 3, 2014, 13 pages.
Response to Non-Final Office Action, U.S. Appl. No. 13/627,825, filed Oct. 21, 2013, 11 pages.
Response to Non-Final Office Action, U.S. Appl. No. 13/627,865, dated Oct. 28, 2013, 17 pages.
Response to Non-Final Office Action, U.S. Appl. No. 13/722,802, filed Mar. 26, 2014, 10 pages.

(56) References Cited

OTHER PUBLICATIONS

Response to Non-Final Office Action, U.S. Appl. No. 29/448,474, dated Mar. 4, 2014, 6 pages.
Response to Non-Final Office Action, U.S. Appl. No. 29/448,467, dated Mar. 4, 2014, 6 pages.
Response to Restriction, U.S. Appl. No. 13/614,372, filed May 16, 2013, 6 pages.
Response to Restriction, U.S. Appl. No. 13/614,508, filed Jun. 1, 2013, 6 pages.
Response to Restriction, U.S. Appl. No. 13/614,577, filed Jun. 1, 2013, 6 pages.
Response to Restriction, U.S. Appl. No. 13/627,812, filed Aug. 7, 2013, 6 pages.
Response to Restriction, U.S. Appl. No. 13/627,825, filed Jun. 1, 2013, 6 pages.
Response to Restriction, U.S. Appl. No. 13/627,850, filed Jun. 1, 2013, 5 pages.
Response to Restriction, U.S. Appl. No. 13/627,865, filed Jun. 1, 2013, 6 pages.
Restriction Requirement, U.S. Appl. No. 13/614,372, mailed Apr. 17, 2013, 6 pages.
Restriction Requirement, U.S. Appl. No. 13/614,508, mailed May 3, 2013, 6 pages.
Restriction Requirement, U.S. Appl. No. 13/614,577, mailed May 2, 2013, 6 pages.
Restriction Requirement, U.S. Appl. No. 13/627,812, mailed Jul. 16, 2013, 7 pages.
Restriction Requirement, U.S. Appl. No. 13/627,825, mailed May 2, 2013, 7 pages.
Restriction Requirement, U.S. Appl. No. 13/627,850, mailed May 2, 2013, 7 pages.
Restriction Requirement, U.S. Appl. No. 13/627,865, mailed May 6, 2013, 5 pages.
Supplemental Amendment After Final Office Action, U.S. Appl. No. 13/614,372, dated Mar. 21, 2014, 7 pages.
US 7,063,700, 06/2006, Michelson (withdrawn).

* cited by examiner

FIG. 1 (Canceled)

FIG. 2 (Canceled)

FIG. 3 (Canceled)

FIG. 4 (Canceled)

FIG. 5 (Canceled)

FIG. 6 (Canceled)

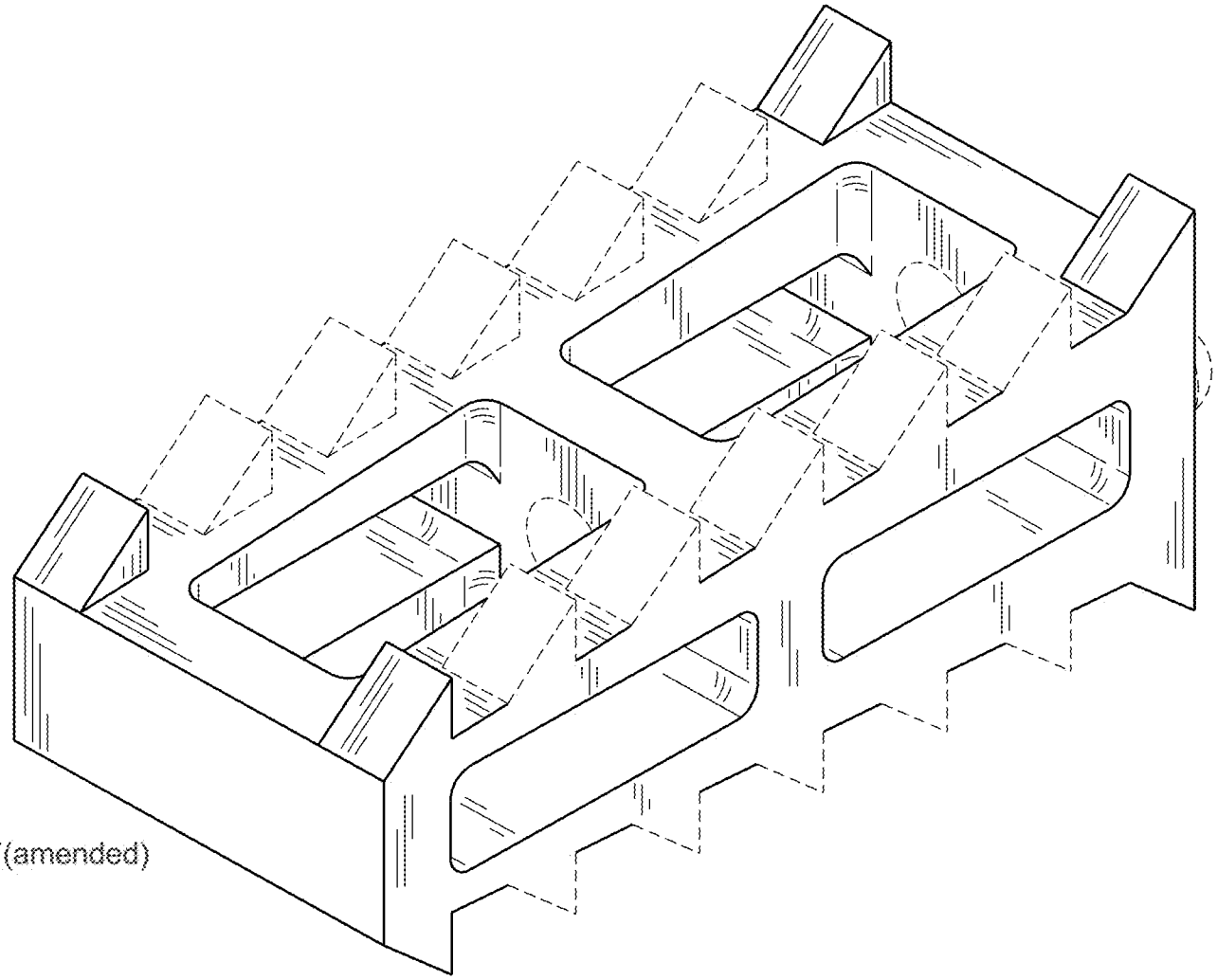
Fig. 7(amended)

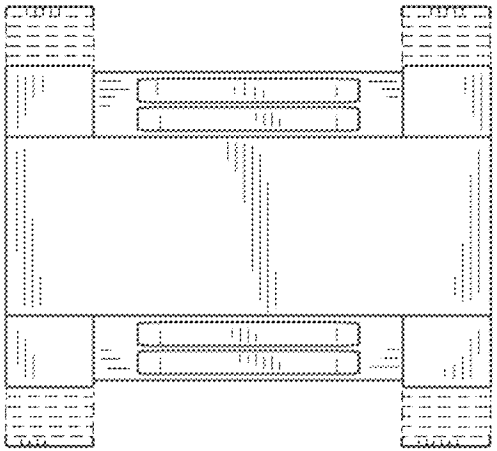
FIG. 8 (Amended)

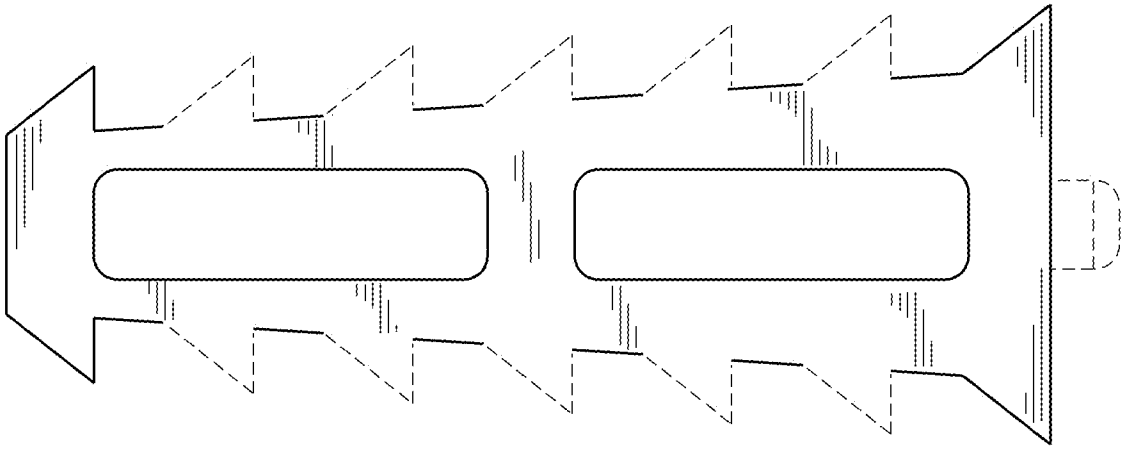
Fig. 9 (amended)

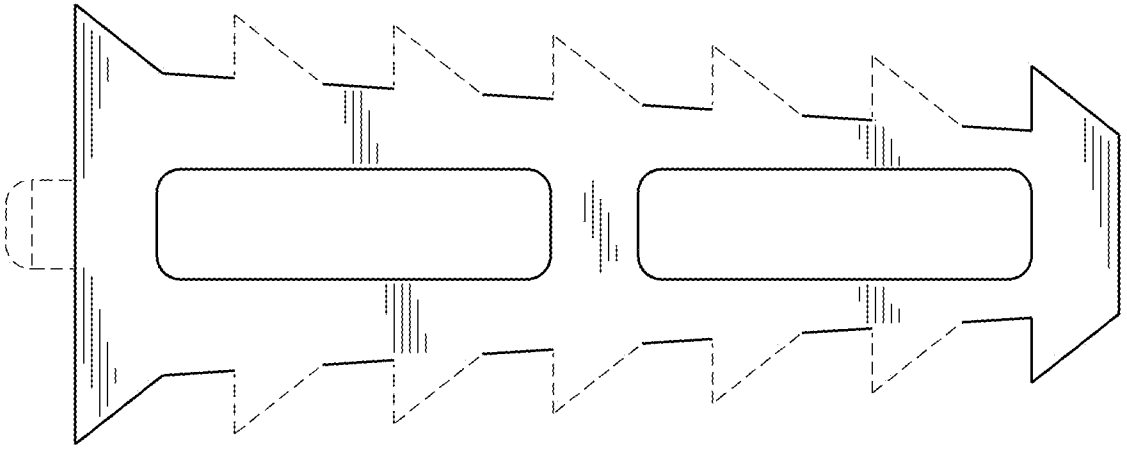
Fig. 10
(amended)

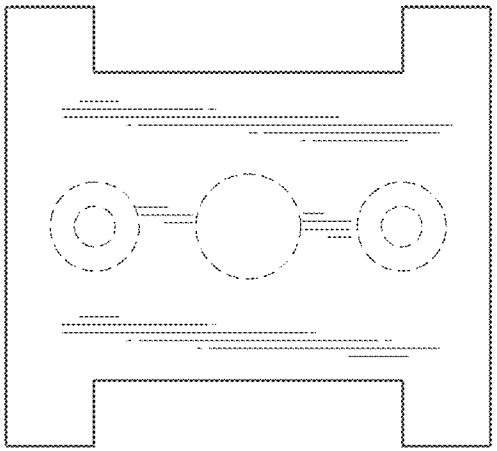
FIG. 11 (Amended)

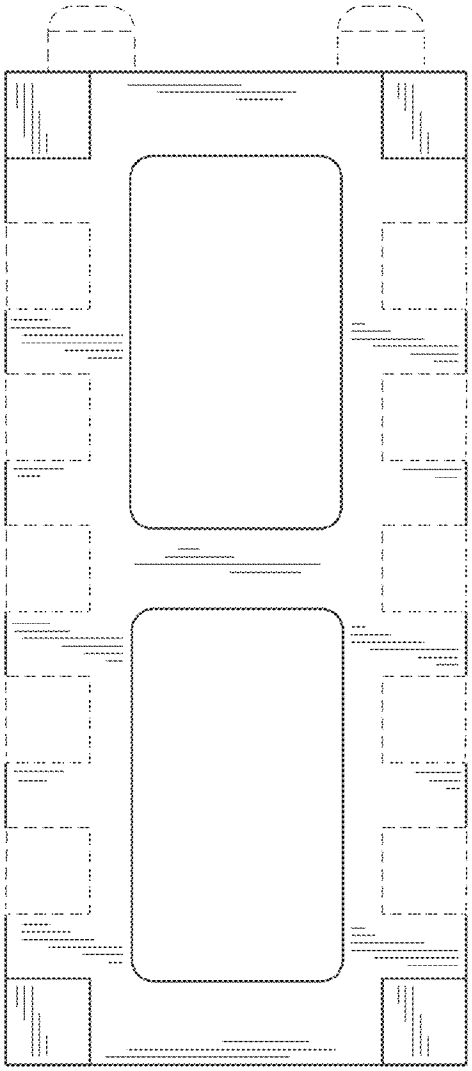
FIG. 12 (Amended)